(12) United States Patent
Bussat et al.

(10) Patent No.: US 11,717,570 B2
(45) Date of Patent: Aug. 8, 2023

(54) GAS-FILLED MICROVESICLES

(71) Applicant: Bracco Suisse SA, Cadempino (CH)

(72) Inventors: Philippe Bussat, Pers-Jussy (FR);
Samir Cherkaoui, Feigeres (FR);
David Lazarus,
Saint-Julien-en-Genevois (FR); Eric Allémann, Troinex (CH); Michel Schneider, Troinex (CH); Christian Guillot, Beaumont (FR)

(73) Assignee: Bracco Suisse SA, Cadempino (CH)

( * ) Notice: Subject to any disclaimer, the term of this patent is extended or adjusted under 35 U.S.C. 154(b) by 0 days.

(21) Appl. No.: 17/610,853

(22) PCT Filed: May 14, 2020

(86) PCT No.: PCT/EP2020/063560
§ 371 (c)(1),
(2) Date: Nov. 12, 2021

(87) PCT Pub. No.: WO2020/229643
PCT Pub. Date: Nov. 19, 2020

(65) Prior Publication Data
US 2022/0211850 A1    Jul. 7, 2022

Related U.S. Application Data

(63) Continuation-in-part of application No. 16/788,083, filed on Feb. 11, 2020, now abandoned, which is a
(Continued)

(51) Int. Cl.
*A61K 41/00* (2020.01)
*A61K 9/127* (2006.01)
(Continued)

(52) U.S. Cl.
CPC ........ *A61K 41/0033* (2013.01); *A61K 9/1271* (2013.01); *A61K 47/12* (2013.01);
(Continued)

(58) Field of Classification Search
None
See application file for complete search history.

(56) References Cited

U.S. PATENT DOCUMENTS 6,139,819 A    10/2000 Unger et al.
8,293,214 B2   10/2012 Swenson et al.
(Continued)

FOREIGN PATENT DOCUMENTS

CN    102614125 A    8/2012
EP    1228770 A1     8/2002
(Continued)

OTHER PUBLICATIONS

International Search Report and Written Opinion for PCT/EP2020/063560, dated Aug. 6, 2020. (Year: 2020).*
(Continued)

*Primary Examiner* — Isaac Shomer
(74) *Attorney, Agent, or Firm* — Vivicar Law, PLLC

(57) ABSTRACT

Lipid formulation particularly for preparing stable gas-filled microvesicles, comprising distearoyl-phosphatidylcholine (DSPC), dipalmitoylphosphatidylethanolamine-PEG5000 (DPPE-PEG5000) and palmitic acid in an advantageous relative molar ratio. The formulation is useful in particular for therapeutic application with ultrasounds.

14 Claims, 1 Drawing Sheet

Related U.S. Application Data continuation-in-part of application No. 16/688,540, filed on Nov. 19, 2019, now abandoned, which is a continuation-in-part of application No. 16/413,526, filed on May 15, 2019, now abandoned.

(51) Int. Cl.
  *A61N 7/00* (2006.01)
  *A61K 47/24* (2006.01)
  *A61K 47/12* (2006.01)
(52) U.S. Cl.
  CPC ............... *A61K 47/24* (2013.01); *A61N 7/00* (2013.01); *A61N 2007/0039* (2013.01)

(56) References Cited

U.S. PATENT DOCUMENTS

| | | | |
|---|---|---|---|
| 9,364,569 B2 | 6/2016 | Schneider et al. | |
| 9,789,210 B1 | 10/2017 | Robinson et al. | |
| 10,588,988 B2 | 3/2020 | Robinson et al. | |
| 11,426,352 B2* | 8/2022 | Bussat | A61K 9/10 |
| 2001/0008626 A1 | 7/2001 | Schneider et al. | |
| 2005/0025710 A1* | 2/2005 | Schneider | A61K 49/225 |
| | | | 424/9.52 |
| 2006/0051297 A1 | 3/2006 | Schneider et al. | |
| 2008/0063603 A1 | 3/2008 | Schneider et al. | |
| 2010/0008863 A1* | 1/2010 | Swenson | A61K 49/223 |
| | | | 530/300 |
| 2010/0008978 A1 | 1/2010 | Drummond et al. | |
| 2011/0200530 A1* | 8/2011 | Allemann | C07K 16/2851 |
| | | | 424/9.1 |
| 2011/0236320 A1 | 9/2011 | Schneider et al. | |
| 2013/0101520 A1 | 4/2013 | Schneider et al. | |
| 2018/0008731 A1 | 1/2018 | Bussat et al. | |

FOREIGN PATENT DOCUMENTS

| | | | |
|---|---|---|---|
| WO | 9409829 A1 | 5/1994 | |
| WO | 9818501 A2 | 5/1998 | |
| WO | 9955383 A2 | 11/1999 | |
| WO | 02055544 A2 | 7/2002 | |
| WO | 2003074005 A2 | 9/2003 | |
| WO | 03084574 A1 | 10/2003 | |
| WO | 2004069284 A2 | 8/2004 | |
| WO | 2007067979 A2 | 6/2007 | |
| WO | 2008075192 A2 | 6/2008 | |
| WO | 2010040772 A2 | 4/2010 | |
| WO | WO-2010040772 A2 * | 4/2010 | ............ A61K 39/44 |
| WO | 2015192093 A1 | 12/2015 | |
| WO | 2016097130 A1 | 6/2016 | |
| WO | 2017117349 A2 | 7/2017 | |

OTHER PUBLICATIONS

International Search Report and Written Opinion for PCT/EP2020/063560, dated Aug. 6, 2020.

SP Scientific, "Basic principles of freeze drying," available at: https://www.spscientific.com/freeze-drying-lyophilization-basics/ (2017).

* cited by examiner

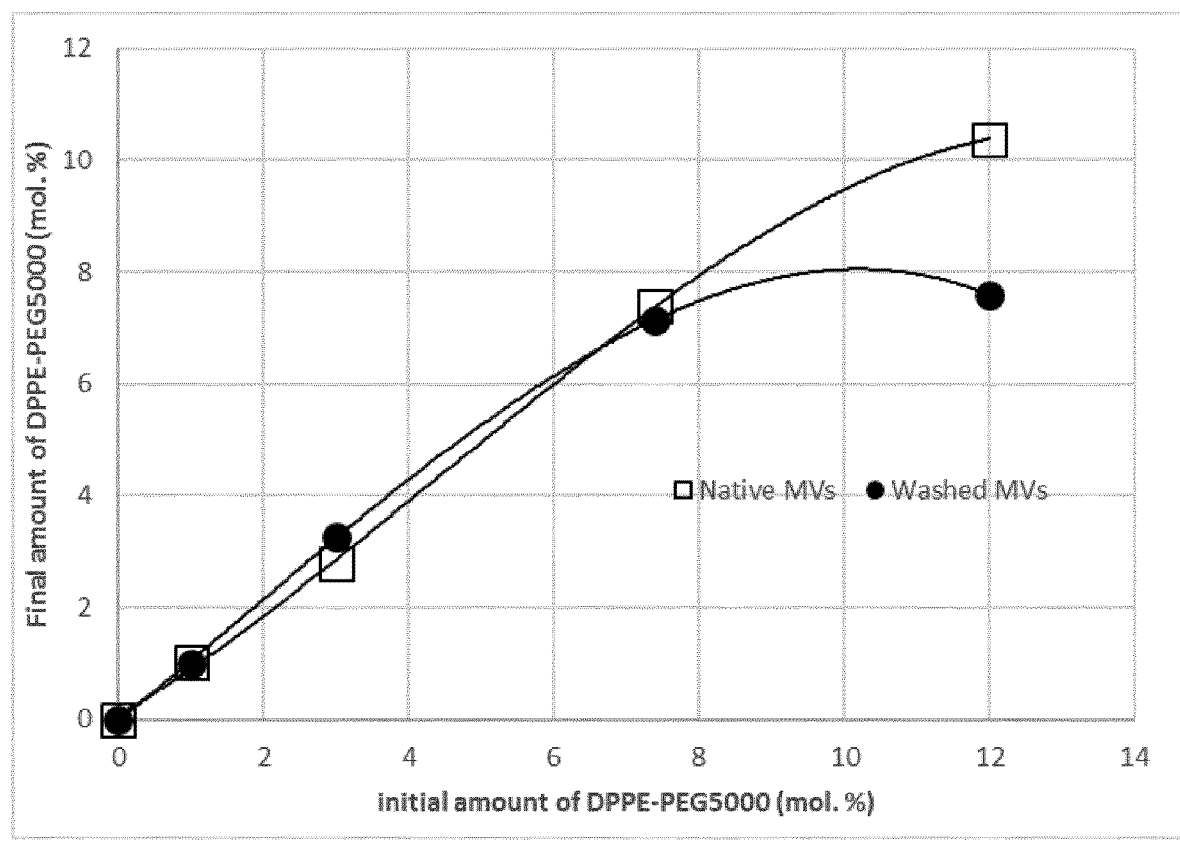

GAS-FILLED MICROVESICLES

CROSS-REFERENCE TO RELATED APPLICATIONS

This application is the national stage application of corresponding international application number PCT/EP2020/063560, filed May 14, 2020, which is a continuation-in-part of U.S. application Ser. No. 16/788,083, filed Feb. 11, 2020, which is a continuation-in-part of U.S. application Ser. No. 16/688,540, filed Nov. 19, 2019, which is a continuation-in-part of U.S. application Ser. No. 16/413,526, filed May 15, 2019, which are hereby incorporated by reference in their entireties.

TECHNICAL FIELD

The invention relates to a new formulation of gas-filled microvesicles, to a method for preparing them and the use of such microvesicles.

BACKGROUND OF THE INVENTION

Rapid development of contrast agents in the recent years has generated a number of different compositions and formulations, which are useful in contrast-enhanced imaging of organs and tissues of human or animal body as well as in therapeutic treatments thereof.

A class of contrast agents particularly useful for Contrast Enhanced UltraSound imaging ("CEUS" imaging) includes suspensions of gas bubbles of nano- and/or micro-metric size dispersed in an aqueous medium. The gas is typically entrapped or encapsulated in a film-layer comprising, for instance, emulsifiers, oils, thickeners or sugars. These stabilized gas bubbles (dispersed in a suitable physiological solution) are generally referred to in the art with various terminologies, depending typically from the stabilizing material employed for their preparation; these terms include, for instance, "microspheres", "microbubbles", "microcapsules" or "microballoons", globally referred to here as "gas-filled microvesicles" (or "microvesicles").

UltraSound Contrast Agents ("USCAs") can be produced according to various manufacturing methods. One of these methods, see e.g. WO94/09829, entails the dissolution of an amphiphilic material (such as a phospholipid and/or fatty acid) and of a freeze-drying protecting compound (e.g. polyetheleneglycol) in an organic solvent; the obtained mixture is then subjected to freeze-drying, typically after being filled into vials, to remove the solvent and obtain a freeze-dried product. Another method, see e.g. WO2004/069284, entails the preparation of a microemulsion of water with a water immiscible organic solvent, said emulsion comprising an amphiphilic material and a freeze-drying protecting compound. The emulsion is then subjected (upon distribution into vials) to a freeze-drying step to remove water and solvent.

The headspace of the vials, containing a freeze-dried solid product in powder form at the bottom thereof, is then filled with a suitable gas (e.g. a fluorinated gas) and finally sealed for storage. Before use, an aqueous suspension of microbubbles is easily prepared by introducing a suitable liquid into the vial (e.g. saline) and gently shaking the vial to dissolve the freeze-dried product.

A commercially available USCA which can be manufactured according to the above method is SonoVue® (or Lumason® in the USA), from Bracco.

Applicant has now found a new formulation particularly suitable for preparing stable gas-filled microvesicles, comprising a combination of 1,2-Distearoyl-sn-glycero-3-phosphocholine (DSPC, also indicated as distearoylphosphatidylcholine), 1,2-dipalmitoyl-sn-glycero-3-phosphoethanolamine-PEG5000 (DPPE-PEG5000, also indicated as dipalmytoylphosphatidylethanolamine-PEG500) and palmitic acid in an advantageous relative molar ratio. The formulation is particularly useful for use in therapeutic applications with ultrasounds.

Schneider et al. (2011), "BR38, a New Ultrasound Blood Pool Agent". *Inv. Radiology*, Vol. 46, Number 8, 486-494, discloses a suspension of phospholipid-stabilized microbubbles obtained by reconstitution of a freeze-dried composition comprising DSPC, DPPE-MPEG5000 and palmitic acid for use as an imaging ultrasound contrast agent.

SUMMARY OF THE INVENTION

The invention relates to a gas-filled microvesicle comprising a mixture of the lipid components (a) 1,2-Distearoyl-sn-glycero-3-phosphocholine (DSPC), (b) 1,2-dipalmitoyl-sn-glycero-3-phosphoethanolamine conjugated with polyethylene glycol having a MW of 5000 g/mol (DPPE-PEG5000) and (c) palmitic acid, wherein said lipid components are in a respective relative molar ratio (a/b/c) of 65-85/4-10/12-22. Preferably the molar ratio is of 70-80/5-9/15-21 and more preferably of about 72-76/6-8/16-20, particularly preferred being a respective molar ratio of 74 (+/−1)/7.5 (+/−0.5)/18.5 (+/−1).

Another aspect relates to a precursor of such gas-filled microvesicle, in the form of a freeze-dried formulation comprising the above lipid components in the above respective molar ratios in admixture with a freeze-drying protecting compound, preferably PEG4000. The total amount of the three lipid components with respect to the amount of freeze-drying protecting compound can be in any range from 0.08% to 0.75% by weight, preferably from 0.10% to 0.50%, more preferably from 0.12% to 0.45%.

In an embodiment, the mixture of the three lipid components is in an amount of from 0.08% to 0.3% by weight with respect to the total amount of the freeze-drying protecting compound, more preferably from about 0.10% to 0.20% by weight, and even more preferably from 0.12% to 0.18% by weight, particularly preferred being an amount of about 0.16% (w/w) with respect to the freeze-drying protecting compound.

In another embodiment, said mixture of the three lipid components is in an amount of from more than 0.3% to 0.5% by weight with respect to the total amount of freeze-drying protecting compound, preferably from 0.35% to 0.45%, more preferably from 0.38% to 0.40% by weight.

Another aspect relates to a sealed vial comprising said freeze-dried formulation in contact with a physiologically acceptable gas, preferably perfluorobutane ($C_4F_{10}$), more preferably in admixture with nitrogen (e.g. 35/65 v/v).

FIGURES

FIG. 1 shows the relative amount of DPPE-PEG5000 in suspensions of native gas-filled microvesicles, compared to the amount of DPPE-PEG5000 in suspensions of washed gas-filled microvesicles, as discussed in Example 3.

DETAILED DESCRIPTION OF THE INVENTION

As used herein the term "DSPC" refers to 1,2-Distearoyl-sn-glycero-3-phosphocholine (also identified as "Distearoylphosphatidylcholine"), while the term DPPE-PEG5000 refers to 1,2-dipalmitoyl-sn-glycero-3-phosphoethanolamine (also identified as "dipalmitoylphosphatidylethanolamine") conjugated with polyethylene glycol having a MW of 5000 g/mol, and more specifically to the methoxy terminated PEG derivative N-(Carbonyl-methoxypolyethyleneglycol 5000)-1,2-dipalmitoyl-sn-glycero-3-phosphoethanolamine or 1,2-dipalmitoyl-sn-glycero-3-phosphoethanolamine-N-[methoxy(polyethylene glycol)-5000] (DPPE-MPEG5000).

Applicant has unexpectedly found that by suitably modulating the respective molar ratios of the lipid components of a composition comprising DSPC, DPPE-PEG and palmitic acid, it is possible to prepare gas-filled microvesicles with improved properties, among others in term of resistance to pressure.

As illustrated in detail in the examples, the Applicant has found in particular that improved characteristics (including higher resistance to pressure) are conferred to gas-filled microvesicles having compositions comprising a molar amount of palmitic acid (with respect to the other two components) of at least 8%, preferably at least 12%, more preferably at least 15% and even more preferably higher than 16%, but not higher than 22%, preferably not higher than 21%, more preferably not higher than 20% and even more preferably lower than 20%. In a particularly preferred embodiment, said amount is of 18.5% (+/−1), more preferably 18.5% (+/−0.5).

Furthermore, as also illustrated in detail in the examples, the Applicant has observed that increasing amounts of DPPE-PEG incorporated into the formulation allow obtaining microvesicles with improved characteristics, such as size distribution (characterized in particular by reduced $D_{V50}$ and $D_N$ values) and lower amounts of large microvesicles (expressed as number of bubbles with size larger than 8 μm). On the other side, Applicant has also observed that molar amounts of DPPE-PEG5000 higher than 8% are often not effectively incorporated into the stabilizing layer of the formed microvesicles. Furthermore, as observed by the Applicant, formulations comprising excessive amounts of DPPE-PEG5000 may result in microvesicles having increasing amounts of large microvesicles. Accordingly, the Applicant has determined that the relative molar amount of DPPE-PEG5000 (with respect to the other two components) shall be of at least 4%, preferably at least 5%, more preferably at least 6% and even more preferably higher than 6%, but not higher than 10%, preferably not higher than 9%, more preferably not higher than 8% and even more preferably lower than 8%. In a particularly preferred embodiment, said amount is of 7.4% (+/−0.5), more preferably 7.4% (+/−0.4).

Concerning DSPC, the Applicant has found that its relative molar amount with respect to the other two components, also considering the above illustrated relative ratios, shall be of at least 65%, preferably at least 70%, more preferably at least 72% and even more preferably higher than 72%, but not higher than 85%, preferably not higher than 80%, more preferably not higher than 76% and even more preferably lower than 76%. In a particularly preferred embodiment, said amount is of 74% (+/−1), more preferably 74% (+/−0.8).

Preferred embodiments of the invention are compositions comprising DSPC/DPPE-PEG/Palmitic acid in a respective molar amount of 65-85/4-10/8-22 (expressed as relative % molar amounts, the total being 100%). Preferably the molar amount is of 70-80/5-8/12-21 and more preferably of about 72-76/6-9/15-20, particularly preferred being a molar ration of 74 (+/−1)/7.5 (+/−0.5)/18.5 (+/−1).

The above formulation is generally prepared as a freeze-dried product, according to a freeze-drying process as illustrated herein. The freeze-dried product comprises a suitable freeze-drying protecting compound, preferably PEG4000. As observed by the Applicant, the amount of freeze-drying protecting compound (particularly PEG4000) with respect to the three lipid components shall be relatively high. In particular, the total amount of the three lipid components with respect to the amount of freeze-drying protecting compound can vary from 0.08% to 0.75% by weight, preferably from 0.10% to 0.50%, more preferably from 0.12% to 0.45%. As observed by the Applicant, this relatively high amount of freeze-drying protecting compound allows a suitably homogeneous dispersion of the components of the formulation in the freeze-dried mass of the component, particularly when prepared according to the manufacturing method disclosed in WO2004/069284.

According to an embodiment, the total weight of the three lipid components of the formulation is from 0.08% to 0.3% by weight with respect to the total amount of freeze-drying protecting compound, preferably from about 0.10% to 0.20% by weight, more preferably from 0.12% to 0.18% by weight, even more preferably of about 0.16%.

According to another embodiment, the total weight of the three lipid components of the formulation is from more than 0.30% to 0.50% by weight with respect to the total amount of freeze-drying protecting compound, preferably from 0.35% to 0.45%, more preferably from 0.38% to 0.40%.

As observed by the Applicant, this latter embodiment is particularly useful for preparing highly concentrated suspensions of gas-filled microvesicles, which may be useful for certain therapeutic applications where it may be desirable to have higher amounts of microvesicles to be administered. As a matter of fact, while higher amounts of injected microvesicles may be achieved by increasing the administered volume of a certain suspension, it may nevertheless be more advisable to administer relatively reduced volumes of suspension having a higher concentration of microvesicles. In principle, higher amounts of gas-filled microvesicles in a suspension can be achieved by increasing the relative amount of lipids in a freeze-dried preparation to be reconstituted. Also, by keeping constant the volume of liquid for reconstituting the freeze-dried product, such higher amounts of lipids would result in a higher concentration of microvesicles in the reconstituted suspension. However, as observed by the Applicant, simply increasing the amount of the lipid components (in the freeze-dried product to be reconstituted) may not necessarily result in a correspondingly higher numbers of microvesicles in the final reconstituted suspension. As a matter of fact, the Applicant has observed that an optimized amount of number of microvesicles with respect to the amount of lipid components in the formulation can be obtained by suitably balancing such amount of lipids with respect to the amount of freeze-drying compound. Particularly advantageous results can thus be obtained when the total weight of the three lipid components of the formulation is from more than 0.30% to 0.50% by weight with respect to the total amount of freeze-drying protecting compound, preferably from 0.35% to 0.45%, more preferably from 0.38% to 0.40%. According to a particular embodiment, the total weight of the three lipid components of the formulation can vary from 1000 μg to 1300 μg, preferably from 1050 μg to 1250 μg, more preferably from 1100 μg to 1200 μg, while the total weight of the freeze-drying protecting compound (PEG4000) can vary from 225 mg to 375 mg preferably from 250 to 350 mg and even more preferably from 275 mg to 325 mg.

As used herein, $D_N$ is the mean diameter in number of a population of microvesicles, while $D_{V50}$ is the median diameter in volume of a said population of microvesicles, indicating that half of the total gas contained in the population is present in microvesicles having a diameter lower than $D_{V50}$. The ratio $D_{V50}/D_N$ provides a general indication about the polydispersity of the population: typically, the lower the $D_{V50}/D_N$ ratio, the narrower the size distribution. The above values of $D_{V50}$, $D_N$ (as well as other parameters such as total number of microvesicles or number of microvesicles larger than 8 μm) can be obtained by measurement with a Coulter counter (e.g. a Coulter Counter Multisizer 3 apparatus fitted with a 30 μm aperture, with a measuring range of 0.7 to 20 μm).

Freeze-Drying Protecting Compound

As defined herein, a freeze-drying protecting compound is a compound with cryoprotective and/or lyoprotective effect. Suitable freeze-drying protecting compounds include, for instance, carbohydrates, e.g. a mono- di- or poly-saccharide, such as sucrose, maltose, trehalose, glucose, lactose, galactose, raffinose, cyclodextrin, dextran, chitosan and its derivatives (e.g. carboxymethyl chitosan, trimethyl chitosan); polyols, e.g. sugar alcohols such as sorbitol, mannitol or xylitol; or hydrophilic polymers, e.g. polyoxyalkylene glycol such as polyethylene glycol (e.g. PEG2000, PEG4000 or PEG8000) or polypropylene glycol. According to an embodiment said freeze-drying protecting compound is polyethylene glycol, preferably PEG4000. PEG4000 as used herein has its normal meaning in the field, indicating a polyethylene glycol having a molecular weight of about 4000 g/mole, in general with a variation of +/−10% around said value.

Preparation of Gas-Filled Microvesicles

A suitable method for preparing suspensions of gas-filled microvesicles comprises the reconstitution, in the presence of a suitable physiologically acceptable gas, of a freeze-dried product comprising the lipid components capable of stabilizing said microvesicles (e.g. by forming a stabilizing layer at the liquid-gas interface) with an aqueous carrier.

The freeze-dried product is typically obtained by freeze-drying a liquid mixture comprising said lipid component and a freeze-drying protecting compound in a suitable solvent.

The liquid mixture which undergoes the freeze-drying process can be obtained according methods know in the art, disclosed e.g. in WO2004/069284.

According to the process disclosed in WO2004/069284, a composition comprising the lipid components may be dispersed in an emulsion of water with a water immiscible organic solvent under agitation, preferably in admixture with a freeze-drying protecting compound. Preferably, an organic solution comprising DSPC and palmitic acid is first prepared which is then emulsified together with an aqueous solution comprising DPPE-PEG5000 and the freeze-drying protecting compound.

Suitable water immiscible organic solvents include, for instance, branched or linear alkanes, alkenes, cyclo-alkanes (e.g. cyclooctane), aromatic hydrocarbons, alkyl ethers, ketones, halogenated hydrocarbons, perfluorinated hydrocarbons or mixtures thereof.

The emulsion may be obtained by submitting the aqueous medium and the solvent, in the presence of the lipid components and freeze-drying protecting compound, to any appropriate emulsion-generating technique known in the art such as, for instance, sonication, shaking, high pressure homogenization, micromixing, membrane emulsification, high speed stirring or high shear mixing. The freeze-drying protecting compound can be added either before or after the formation of the emulsion, e.g. as an aqueous solution comprising such freeze-drying protecting compound. The so obtained microemulsion, which contains microdroplets of solvent surrounded and stabilized by the lipid components, is then freeze-dried according to conventional techniques to obtain a freeze-dried material, which can then be used for preparing a suspension of gas-filled microvesicles.

For the freeze-drying process, the emulsion containing the lipid components and the freeze-drying protecting compound (obtained e.g. according to the previously illustrated manufacturing processes), is typically sampled into glass vials (e.g. DIN/ISO 8362 crimp vials, of various dimensions) which are loaded into a freeze-dryer. As observed by the Applicant, introducing an excessive volume of the microemulsion to be freeze-dried into a vial may however cause cracks in the vial during the freeze-drying process. Thus, for instance, a DIN 8R vial (volume of approx. 11.5 mL) shall preferably be filled with a volume of less than 2 mL of microemulsion, preferably not more than 1.5 mL. Such relatively low volumes necessarily limit the total amount of lipid components which can be introduced into the vial, with a consequent limited number of gas-filled microvesicles obtainable upon reconstitution of the freeze-dried product. Thus, if larger amounts of microvesicles are needed in a single vial, vials with larger capacity shall be used. For instance, DIN20R vials (having a capacity of about 25 mL) may be filled with up to 4 mL of microemulsion, preferably not more than 3 mL, without undergoing cracks during the freeze-drying process.

The freeze-drying process generally includes an initial step (primary drying) where the vials are rapidly deep-cooled (e.g. at temperatures of from −35° C. to −70° C.) to freeze the liquid(s) of the mixture and then subjected to vacuum (e.g. 0.1-0.8 mbar); during the primary drying, the substantial totality of the frozen liquid(s) (e.g. water and/or solvents) is removed by sublimation, typically up to about 95% of the total amount of liquid, preferably up to about 99%. After the primary drying, residual liquid (including possible interstitial water) can be further removed during the secondary drying, which is typically conducted at a temperature higher than room temperature, under vacuum (preferably by maintaining the same vacuum applied during the primary drying). The temperature during the secondary drying is preferably not higher than 35° C. The secondary drying can be stopped when the residual content of the liquid(s) reaches a desired minimum value, e.g. less 3% (preferably less than 1%) by weight of water with respect to the total mass of residual freeze-dried product, or e.g. less than 0.01% by weight, preferably less than 0.08%, for residual solvent(s).

After completion of the freeze-drying process (i.e. stopping of heating and vacuum removal), the freeze-dried product can undergo an additional thermal treatment step. Preferably the thermal treatment is performed on the sealed vial, after saturating the headspace of the vials containing the freeze-dried product with a suitable physiologically acceptable gas and then stoppering (e.g. with a rubber, such as butyl rubber, stopper) and sealing (e.g. with a metal, such as aluminium, crimp seal) the vials. In this case, the vials are preferably removed from the freeze-drier and introduced in a suitable oven for the thermal treatment. Alternatively, such thermal treatment can be performed on the open vial (which is preferably kept into the freeze-dryer), which is then saturated with the gas and then stoppered/sealed.

Examples of suitable physiologically acceptable gases include, for instance, fluorinated gases such as $SF_6$, $C_3F_8$, $C_4F_{10}$, optionally in admixture with air or nitrogen.

Preferably $C_4F_{10}$, or a mixture of $C_4F_{10}$ with nitrogen, is used in combination with a lipid mixture comprising DSPC, DPPE-PEG5000 and palmitic acid, as above defined.

As observed by the Applicant, said additional heat treatment of the freeze-dried product surprisingly results in improved characteristics of the suspension of gas-filled microvesicles obtained upon reconstituting of the freeze-dried product, with respect to suspensions obtained from freeze-dried products which do not undergo such heat treatment.

Applicant observed in particular that such treatment results in an increased resistance to pressure of the obtained microvesicles.

The freeze-dried product is preferably heated at a temperature higher than 35° C. (e.g. 36° C.), more preferably at a temperature of 38° C. or higher. The maximum temperature of the heat treatment generally depends on the materials comprised in the freeze-dried product. For instance, such temperature shall be lower than the melting point of the material used as freeze-drying additive, which is the component forming most of the mass of the freeze-dried product (typically from 50 up to more than 600 times the weight of the active components forming the stabilizing layer of the microvesicles). For instance, PEG4000 has a melting temperature of 53-58° C. According to an embodiment, the heating temperature is preferably of 50° C. or lower. Preferred temperatures for the heat treatment are from 38° C. to 45° C.

The duration of the heat treatment generally depends on the temperature of the treatment; typically, the higher the temperature, the shorter the duration of the heating. As the materials forming the gas-filled microvesicles envelope (phospholipids in particular) may undergo degradation reaction if subjected to excessive temperatures for a too long period of time (with possible negative consequences on the characteristics of the reconstituted microvesicles), the duration of the heat treatment shall not be unnecessarily prolonged. While a treatment duration of about 8 hours may be sufficient (particularly in combination with temperatures higher than 45° C., e.g. 48° C.), the duration of the heat treatment is preferably performed for 12 hours, up to e.g. 20 hours, more preferably 14 to 18 hours. While in particular cases longer durations may well be applied (e.g. in combination with temperatures lower than 45° C., preferably lower than 42° C.), the Applicant has observed that the characteristics of the final gas-filled microvesicles are only slightly if not at all further improved; such increased duration is thus in most cases not necessary and generally inconvenient in terms of manufacturing economy at the industrial scale.

The thermal treatment has been proven to be particularly effective for improving the characteristics of gas-filled microvesicles obtained by reconstituting a freeze-dried product comprising a mixture of lipid components as defined above with a freeze-drying protective compound. Preferably, said freeze-dried product is heated at a temperature of from about 36° C. to 45° C., particularly of about 39° C. (+/−3° C.) for at least eight hours, preferably for about 15 h (+/−5 h).

As mentioned above, the thermal treatment of the freeze-dried product results in an increased resistance of the gas-filled microvesicles to pressure. Advantageously, microvesicles with increased resistance to pressure generally show an increased time persistency in the blood stream once injected.

Resistance to pressure of gas-filled microvesicles can be assessed by determining the empiric parameter "Pc50" or "critical pressure".

As explained in detail in the experimental part, the Pc50 of a suspension of gas-filled microvesicles identifies the value of applied overpressure (with respect to atmospheric pressure) at which the absorbance of a suspension of microvesicles drops to half of the absorbance of the suspension measured at atmospheric pressure, said applied overpressure resulting in a substantial reduction of the population of microvesicles with respect to the initial one (at atmospheric pressure). As a matter of fact, reduction of the absorbance of a suspension of microvesicles is related to the reduction of the initial population of gas-filled microvesicles, whereby the initially milky suspension (high concentration of microvesicles) becomes more and more transparent under increasing pressure (reduced concentration due to collapse of microvesicles). The higher the Pc50 values, the higher the resistance to pressure of microvesicles. For ultrasound diagnostic applications, a minimum Pc50 value of at least 12 kPa (about 90 mmHg) is desirable for gas-filled microvesicles, preferably at least 13 kPa (about 100 mmHg), more preferably at least 14 kPa (105 mmHg). For ultrasound therapeutic applications, generally needing longer persistence time in the blood flow, a minimum Pc50 value of at least 55 kPa (about 412 mmHg) is desirable, preferably at least 70 kPa (about 525 mmHg), more preferably at least 80 kPa (about 600 mmHg), while higher values of Pc50 are even more preferred.

Typically, the thermal treatment of the freeze-dried product allows increasing the Pc50 of the reconstituted suspension of microvesicles of at least 5 kPa, preferably at least 8 kPa and more preferably at least 10 kPa with respect to the Pc50 of a reconstituted suspension obtained from a freeze-dried product which has not been submitted to such thermal treatment. Such increase of Pc50 may be up to 15 kPa and in some embodiments up to 25 kPa.

In particular, a suspension of microvesicles reconstituted from a freeze-dried product as defined herein and subjected to a thermal treatment as defined above has a value of Pc50 of at least 75 kPa, preferably of at least 80 kPa and more preferably of at least 90 kPa, up to e.g. 110 kPa, preferably up to 105 kPa.

Suspension of Gas-Filled Microvesicles

The suspension of gas-filled microvesicles can then be prepared by reconstituting the freeze-dried product with a physiologically acceptable (aqueous) carrier, under gentle agitation. Suitable physiologically acceptable (aqueous) carriers include, for instance, water for injection, saline or glucose solution, optionally containing excipients or additives such as pH regulators, osmolality adjusters, viscosity enhancers.

Pharmaceutical Kit, Administration and Methods of Use

The vials containing the freeze-dried product can be advantageously packaged in a two-component diagnostic and/or therapeutic kit, preferably for administration by injection. The kit preferably comprises the vial containing the freeze-dried product and a second container (e.g. a syringe barrel) containing the physiologically acceptable aqueous carrier for reconstitution. In an embodiment, the vial is a DINER glass vial (or equivalent) containing from about 50 to about 150 mg of freeze-dried product; preferably, the amount of lipid components with respect to the freeze-drying compound is from 0.10% to 0.30% by weight. In another embodiment, the vial is a DIN20R vial (or equivalent) containing from about 250 to 350 mg of freeze dried product; preferably, the amount of lipid components with respect to the freeze-drying compound is from more than 0.30% to 0.50% by weight. The volume of aqueous carrier for reconstitution is typically of about 5 mL. For certain therapeutic applications, the suspension obtained from the reconstitution of the freeze-dried product in the DIN20R vials may be admixed with a volume (e.g. 50 mL) of a physiologically acceptable liquid for injection (e.g. saline), for a sustained administration of the suspension.

The microvesicles of the present invention may be used in a variety of diagnostic and/or therapeutic techniques, including in particular ultrasound.

Therapeutic techniques include any method of treatment of a patient which comprises the combined use of ultrasounds and gas-filled microvesicles either as such (e.g. in ultrasound mediated thrombolysis, high intensity focused ultrasound ablation, blood-brain barrier permeabilization, immunomodulation, neuromodulation, radiosensitization) or in combination with a therapeutic agent (i.e. ultrasound mediated delivery, e.g. for the delivery of a drug or bioactive compound to a selected site or tissue, such as in tumor treatment, gene therapy, infectious diseases therapy, metabolic diseases therapy, chronic diseases therapy, degenerative diseases therapy, inflammatory diseases therapy, immunologic or autoimmune diseases therapy or in the use as vaccine), whereby the presence of the gas-filled microvesicles may provide a therapeutic effect itself or is capable of enhancing the therapeutic effects of the applied ultrasounds, e.g. by exerting or being responsible to exert a biological effect in vitro and/or in vivo, either by itself or upon specific activation by various physical methods (including e.g. ultrasound mediated delivery).

Microvesicles according to the invention can typically be administered for therapeutic purposes in a concentration of from about 0.01 to about 5.0 μL of gas per kg of patient, depending e.g. from their respective composition, the type of subject under treatment, the tissue or organ to be treated and/or the therapeutic method applied.

In an embodiment said method of ultrasound therapeutic treatment comprises:
(i) administering to a patient a suspension of gas-filled microvesicles obtained by reconstitution of a freeze-dried product obtained according to the process of the invention;
(ii) identifying a region of interest in said patient to be submitted to a therapeutic treatment, said region of interest comprising said suspension of gas-filled microvesicles; and
(iii) applying an ultrasound beam for therapeutically treating said region of interest;
whereby said ultrasound therapeutic treatment is enhanced by the presence of said suspension of gas-filled microvesicles in said region of interest.

Said suspension of microvesicles has preferably a value of Pc50 of at least 84 kPa, more preferably at least 88 kPa and even more preferably of at least 90 kPa, up to about e.g. 105 kPa.

The following examples will help to further illustrate the invention.

EXAMPLES

Materials
DSPC: 1,2-distearoyl-sn-glycero-3-phosphocholine (Distearoylphosphatidylcholine)
DPPE-PEG5000: 1,2-dipalmitoyl-sn-glycero-3-phosphoethanolamine-N-[methoxy(polyethylene glycol)-5000] (ammonium salt)
PEG4000=Polyethylene glycol (MW=4000 g/mol)

Measurement of Pressure Resistance (Pc50)

The resistance to pressure of gas-filled microvesicles was evaluated using an in-house developed pressure nephelometer. Briefly, the microvesicles suspension was introduced into a spectrophotometer sample cell (airtight and connected to a pressurization system). The optical density (absorbance at 700 nm) of the suspension is continuously recorded while linearly increasing the pressure applied to the sample in the cell from atmospheric pressure (760 mmHg, 101.3 kPa) to an over pressure of two bars (2280 mmHg, 303.9 kPa), at a rate of about 4 mmHg/s (533 Pa/s).

The Pc50 parameter ("critical pressure", expressed in kPa) characterizing each suspension identifies the overpressure (with respect to atmospheric pressure) at which the absorbance of the microvesicles suspension drops to half of its initial value.

Determination of Parameters of Gas-Filled Microvesicles

The size distribution parameters (Dv50 and Dn, expressed in μm), the number of the microvesicles (expressed as particles/mL of suspension) and the percentage of microvesicles with diameter larger than 8 μm (expressed as percentage of particles over the total amount of particles) were determined by using a Coulter Counter Multisizer 3 apparatus fitted with a 30 μm aperture with a measuring range of 0.7 to 20 μm. 50 μL of microbubble samples were diluted in 100 ml of saline at room temperature and allowed to equilibrate for 3 minutes prior to measurement.

Example 1

Preparation of DSPC/Palmitic Acid/DPPE-PEG Containing Microvesicles
(a) 25 mg of a DSPC/Palmitic acid mixture (80/20 molar ratio) are dissolved in cyclooctane (4 mL), at 70° C. for 5 minutes.
(b) Separately, DPPE-PEG5000 (16.7 mg, 7.4% molar with respect to the molar amount of total lipid components) was dissolved in distilled water (1 mL) at 70° C. and a 10% (w/w) PEG4000 solution in distilled water (49 mL) was added thereto.
(c) The aqueous and organic phases were emulsified (Megatron MT3000, 10'000 rpm, 3.5 min). The emulsion was recovered in a 100 mL flask (Duran), then heated at 80° C. for 1 hour and finally cooled to room temperature (~1 h).
(d) The emulsion was then diluted five folds with the above 10% PEG4000 solution (i.e., 216 mL of 10% PEG4000 solution were added to the 54 mL of the emulsion) and sampled in DINER vials (0.75 mL/vial).

The relative DSPC/Palmitic acid/DPPE-PEG5000 molar ratio in the emulsion was of about 74/18.5/7.5. The total weight of the three components with respect to the total amount of PEG4000 is of about 0.16%.

The vials were cooled at −50° C. under vacuum and then subjected to lyophilization, followed by secondary drying above room temperature until complete removal of water and solvent (less than 0.5% by weight), as described in example 1. At the end of the freeze-drying process, the headspace of the vials is saturated with a 35/65 mixture of $C_4F_{10}/N_2$ and the vials are stoppered and sealed.

The vials were then heated at 38° C. for 16 hours.

The product in the vial was then redispersed in saline (5 mL/vial) upon gentle shaking before use.

Example 2

Effect of Different Concentrations of Palmitic Acid

Example 1 was repeated, by modifying the relative molar amount of palmitic acid with respect to DSPC (i.e. 0, 10, 20, 40 and 60, respectively), maintaining the same amount of DPPE-PEG5000. This corresponds to relative molar amounts of palmitic acid of about 0%, 9.3%, 18.5%, 37.1% and 55.6% in the final formulation.

Results are reported in the following table 1, showing that amounts of palmitic acid between 10 and 20 provide microvesicles with improved characteristics, particularly in terms of pressure resistance, number of microvesicles and size distribution. Considering all the characteristics, formulations with a molar amount of palmitic acid of about 20% w/r to DSPC are particularly preferred.

TABLE 1

Effect of Palmitic acid molar amount (w/r to DSPC)

| Amt Palm. Acid | Dv50 (μm) | Dn (μm) | Nb Mv/mL | Pc50 (kPa) |
| --- | --- | --- | --- | --- |
| 0 | 4.04 | 1.53 | 1.72E+08 | 68.39 |
| 10 | 3.86 | 1.47 | 1.97E+08 | 75.86 |
| 20 | 3.86 | 1.50 | 1.98E+08 | 75.59 |
| 40 | 4.07 | 1.53 | 1.90E+08 | 63.59 |
| 60 | 3.66 | 1.49 | 1.81E+08 | 58.93 |

Example 3

Effect of Different Concentrations of DPPE-PEG5000

Example 1 was repeated by varying the molar amount of DPPE-PEG5000 (0, 1%, 3%, 7.4%, 12%, with respect to the total molar amount of lipid components), by maintaining the same amount and ratio of DSPC/palmitic acid.

Results are illustrated in Table 2 showing that an amount of DPPE-PEG5000 around 7.4% provides preparation with a reduced number of microvesicles having a diameter larger than 8 microns (Nb Mv>8 μm), as well as narrower distribution.

TABLE 2

Different amounts of DPPE-PEG5000

| Concentration of DPPE-PEG5000 Mol % | Dv50 (μm) | Dn (μm) | Nb Mv > 8 μm (%) |
| --- | --- | --- | --- |
| 0 | 10.28 | 1.26 | 0.517 |
| 1 | 3.99 | 1.42 | 0.100 |
| 3 | 3.94 | 1.50 | 0.102 |
| 7.4 | 3.65 | 1.48 | 0.060 |
| 12 | 3.65 | 1.47 | 0.079 |

The above preparations (native microvesicles) were then submitted to two washing steps, to remove components not forming the stabilizing layer of the microvesicles. As inferable from FIG. 1, while the amount of DPPE-PEG5000 is substantially similar in the native suspension and in the washed suspension up to a concentration of 7.4% (indicating that the DPPE-PEG is incorporated into the stabilizing layer of the microvesicles at the desired molar amount), at higher concentrations the amount of DPPE-PEG5000 in the washed suspension is much lower than the one in the native suspension, indicating that the stabilizing layer is substantially unable to incorporate DPPE-PEG5000 in too much excess with respect to 7.4%). For this reason, a too large excess, e.g. higher than 10% is not desirable and amounts of 9% or lower, preferably of 8% or lower are desirable.

Example 4

Effect of Different Amounts of PEG4000

Example 1 was repeated, but the PEG4000 solution used for the five-fold dilution of the emulsion in step (d) was used at different concentrations, namely 2%, 5%, 10%, 15% and 20% by weight; the total weight of the lipid components with respect to the amount of PEG4000 was thus of about 0.77%, 0.31%, 0.16%, 0.10% and 0.08%, respectively.

Results are illustrated in table 3, showing that the use of solutions of PEG4000 at concentrations higher than 2% or lower than 20% by weight, for the five-fold dilution of the emulsion prior to freeze-drying (resulting in compositions where the total weight of the three components with respect to the total amount of PEG4000 is lower than 0.77% and higher than 0.08%), provide suspensions of gas-filled microvesicles with particularly advantageous characteristics (such as relative narrow size distribution, improved pressure resistance and in particular a lower number of large size microvesicles).

TABLE 3

Different amounts of PEG4000

| Conc. of PEG4000 solution (% by weight) | Dv50 (μm) | Dn (μm) | Nb Mv > 8 μm (%) | Pc50 (kPa) |
| --- | --- | --- | --- | --- |
| 2 | 3.90 | 1.35 | 0.084 | 66.26 |
| 5 | 4.00 | 1.50 | 0.082 | 76.13 |
| 10 | 3.78 | 1.53 | 0.065 | 79.06 |
| 15 | 3.75 | 1.51 | 0.076 | 79.86 |
| 20 | 3.92 | 1.49 | 0.120 | 76.66 |

Example 5

Effect of Emulsion Dilution

Example 1 was repeated, but the dilution of the emulsion at step (d) was changed. In a first batch, the emulsion was sampled in vials without dilution (in this case the total weight of the lipid components with respect to the amount of PEG4000 was 0.78%). In a second batch, the emulsion was diluted two-fold (54 mL emulsion+54 mL PEG4000 10% solution) and then sampled in vials (in this case the total weight of the lipid components with respect to the amount of PEG4000 was 0.39%). These two batches were compared with the preparation of example 1, with the five-fold dilution of the emulsion (in this case the total weight of the lipid components with respect to the amount of PEG4000 was 0.16%). Results are illustrated in table 4.

TABLE 4

Influence of emulsion dilution in PEG4000 10% solution

| Dilution | Dv50 (μm) | Dn (μm) | Nb Mv > 8 μm (%) | Pc50 (kPa) |
| --- | --- | --- | --- | --- |
| no | 4.86 | 1.51 | 0.207 | 79.99 |
| Two-fold | 3.79 | 1.47 | 0.059 | 88.12 |
| Five-fold | 3.78 | 1.53 | 0.065 | 79.06 |

As inferable from the data in table 4, preparations obtained with a two-fold dilution of the emulsion with a 10%

(w/w) PEG4000 solution before freeze-drying (the total weight of the lipid components with respect to the amount of PEG4000 being of 0.39%) provides suspensions of gas filled microvesicles with improved properties with respect to preparations where there was no dilution (amount of lipids 0.78%) or a five-fold dilution (amount of lipids 0.16%), Furthermore, the number of microvesicles per µg of lipid components was of $9.48 \cdot 10^6$ for the two-fold dilution preparation, while only of $6.68 \cdot 10^6$ for the no-dilution preparation and $7.76 \cdot 10^6$ for the five-fold dilution preparation; these results show that by suitably balancing the ratio lipid components vs PEG4000 it is possible to optimize the number of microvesicles which can be formed by a determined amount of lipid components.

Example 6

Pilot Scale Preparation

Example 1 was repeated at a pilot scale (amounts of materials are about 50 times those of the lab-scale experiments), with the difference that the step (d) was performed with a two-fold dilution of the emulsion with 10% (w/w) PEG4000 solution.

The final emulsion was sampled in DIN20R glass vials (3 mL emulsion/vial), for a total amount of about 300 mg PEG4000 per vial and a respective amount of about 0.39% by weight of lipid components.

After freeze-drying and reconstitution in saline, the following results were determined:
Total number of microvesicles: $13 \cdot 10^9$
Number of microvesicles/µg of lipids: $1.12 \cdot 10^7$
Dv50 (µm): 3.7
Dn (µm): 1.48
Nb Mv>8 µm (%): 0.06

Example 7

Preparation of Freeze-Dried Product (7a-7h)

The procedure illustrated in the working examples of WO2004/069284 was used for preparing eight different batches (7a-7h) each consisting of several vials containing the freeze-dried product.

Briefly, an emulsion of cyclooctane and water (about 1.5/100 v/v) containing about 90 mg/L of DSPC, 7 mg/L of palmitic acid, 60 mg/L of DPPE-PEG5000 (molar ratio of about 75/18/7) and 100 g/L of PEG4000 is prepared (Megatron MT3000, Kinematica; 10'000 rpm, 3.5 min) and sampled into DINER vials (about 1 mL/vial).

The vials were cooled at −50° C. under vacuum and then subjected to lyophilization, followed by secondary drying above room temperature until complete removal of water and solvent (less than 0.5% by weight), as described in example 1. At the end of the freeze-drying process, the headspace of the vials is saturated with a 35/65 mixture of $C_4F_{10}/N_2$ and the vials are stoppered and sealed.

The different batches (7a to 7h) were used for the subsequent heat treatment experiments.

Example 8

Effect of the Heat Treatment on Batches Manufactured According to Example 7

The vials of the various batches (7a-7h) prepared according to example 7 were submitted to different heat treatments and the effect on the characteristics of the reconstituted suspensions of gas-filled microvesicles were observed.

Experiment 8.1

The vials of batch 7a were submitted to a heating temperature of 40° C. or 45° C. for 16 hours or not heated. The product in the vial was then reconstituted with 5 ml of saline and the characteristics of the microvesicles in the suspension were measured. Results are reported in the following table 5.

TABLE 5

| Batch 7a | |
| --- | --- |
| Heat Treatment for 16 h | Pc50 (kPa) mean value |
| No heating | 66.1 |
| 40° C. | 84.8 |
| 45° C. | 78.8 |

As inferable from the above data, a substantial increase in the pressure resistance is obtained upon heat treatment also for batches manufactured according to the procedure of example 7.

Experiment 8.2

The vials of batch 7b were submitted to a heating temperature of 40° C. for a time ranging from 16 to 88 hours, or not heated. The product in the vial was then reconstituted with 5 ml of saline and the characteristics of the microvesicles in the suspension were measured. Results are reported in the following table 6.

TABLE 6

| Batch 7b | |
| --- | --- |
| Heating time T = 40° C. | Pc50 (kPa) mean value |
| No heating | 82.1 |
| 16 hours | 99.0 |
| 40 hours | 103.6 |
| 64 hours | 98.6 |
| 88 hours | 102.5 |

As inferable from the above data, a substantial increase in the pressure resistance is obtained upon heat treatment at 40° C. A duration of the treatment of 16 h is generally considered sufficient, also for avoiding possible negative effects caused by longer thermal treatments on other characteristics of the microvesicles (e.g. increase of large size microvesicles in the reconstituted suspension).

Experiment 8.3

The vials of batches 7c-7g were submitted to a heating temperature of 40° C. for a period of 16 hours, or not heated. The product in the vial was then reconstituted with 5 mL of saline and the characteristics of the microvesicles in the suspension were measured. Results are reported in the following table 5.

TABLE 5

| Batches 7c-7g (40° C., 16 h) | | |
| --- | --- | --- |
| Batch No. | Thermal Treatment | Pc50 (kPa) mean value |
| 7c | No | 70.6 |
| 7c | Yes | 93.7 |
| 7d | No | 74.1 |
| 7d | Yes | 94.3 |
| 7e | No | 69.6 |

TABLE 5-continued

Batches 7c-7g (40° C., 16 h)

| Batch No. | Thermal Treatment | Pc50 (kPa) mean value |
|---|---|---|
| 7e | Yes | 94.2 |
| 7f | No | 62.8 |
| 7f | Yes | 79.8 |
| 7g | No | 55.4 |
| 7g | Yes | 81.3 |

As inferable from the above table, for the suspensions of microvesicles reconstituted from the various batches an increase in pressure resistance of more than 15 kPa or more and up to about 25 kPa is obtained after heat treatment of the freeze-dried products.

Experiment 8.4

The vials of batch 7h were submitted to a heat treatment at 38° C. for a time ranging from two to 24 hours. The product in the vial was then reconstituted with 5 mL of saline and the characteristics of the microvesicles in the suspension were measured. Results are reported in the following table 6.

TABLE 6

Batch 7h

| Heating time (h) at 38° C. | Pc50 (kPa) mean value |
|---|---|
| 0 | 63.19 |
| 2 | 73.33 |
| 4 | 74.66 |
| 6 | 79.33 |
| 8 | 80.26 |
| 12 | 82.66 |
| 16 | 79.73 |
| 24 | 83.06 |

As inferable from the above table, an increasing pressure resistance of the microvesicles in the reconstituted suspension is obtained upon heating the freeze-dried material for an increasing time, up to 8-12 hours at 38° C. Further heating of the material (16 or 24 hours) does not substantially further increase the pressure resistance.

The invention claimed is:

1. A freeze-dried formulation, for preparing gas-filled microvesicles, comprising a mixture of the following lipid components: (a) distearoyl-phosphatidylcholine (DSPC), (b) dipalmitoylphosphatidyl-ethanolamine conjugated with polyethyleneglycol having a Mw of 5000 g/mol (DPPE-PEG5000) and (c) palmitic acid; said lipid components being in a respective molar amount a/b/c of 65 to 85/4 to 10/8 to 22, wherein the formulation further comprises polyethylene glycol 4000 g/mol (PEG4000), and wherein the mixture of lipid components has a weight of from more than 0.3% to 0.5% with respect to the weight of PEG4000.

2. The freeze-dried formulation of claim 1 wherein said respective molar amount is of 70-80/5-8/12-21.

3. The freeze-dried formulation of claim 1 wherein said respective molar amount is of 72-76/6-9/15-20.

4. The freeze-dried formulation of claim 1 wherein said respective molar amount is of 74 (+/−1)/7.5 (+/−0.5)/18.5 (+/−1).

5. The freeze-dried formulation of claim 1 wherein said weight is from 0.35% to 0.45% by weight.

6. The freeze-dried formulation of claim 1 wherein said weight is from 0.38% to 0.40% by weight.

7. A sealed vial comprising from about 250 mg to about 350 mg of the freeze-dried formulation according to claim 1.

8. A suspension of gas-filled microvesicles wherein said microvesicles comprise a mixture of lipid components DSPC, DPPE-PEG and palmitic acid in a respective molar amount of 65-85/4-10/8-22, wherein the suspension further comprises PEG4000, and wherein the mixture of lipid components has a weight of from more than 0.3% to 0.5% with respect to the weight of PEG4000.

9. The suspension of claim 8 wherein said respective molar amount is of 70-80/5-8/12-21.

10. The suspension of claim 8 wherein said respective molar amount is of 72-76/6-9/15-20.

11. The suspension of claim 8 wherein said respective molar amount is of 74 (+/−1)/7.5 (+/−0.5)/18.5 (+/−1).

12. The suspension of gas-filled microvesicles of claim 8 wherein said weight is from 0.35% to 0.45% by weight.

13. The suspension of gas-filled microvesicles of claim 8 wherein said weight is from 0.38% to 0.40% by weight.

14. A method of ultrasound therapeutic treatment comprising:
(i) administering to a patient a suspension of gas-filled microvesicles as defined in claim 8 and a therapeutic agent;
(ii) identifying a region of interest in said patient to be submitted to a therapeutic treatment, said region of interest comprising said suspension of gas-filled microvesicles; and
(iii) applying an ultrasound beam for therapeutically treating said region of interest;
whereby said ultrasound therapeutic treatment is enhanced by the presence of said suspension of gas-filled microvesicles in said region of interest.

* * * * *